United States Patent
Farmilo et al.

[19]

[11] Patent Number: 5,965,454
[45] Date of Patent: Oct. 12, 1999

[54] AUTOMATED HISTO-CYTOCHEMISTRY APPARATUS AND ENCAPSULATION SYSTEM FOR PROCESSING BIOLOGICAL MATERIALS

[75] Inventors: A. James Farmilo, Oakville; Ronald H. Stead, Bowmanville, both of Canada

[73] Assignee: Histaggen Incorporated, Bowmanville, Canada

[21] Appl. No.: 08/850,310

[22] Filed: May 5, 1997

Related U.S. Application Data

[62] Continuation-in-part of application No. 08/439,315, May 11, 1995, abandoned, which is a continuation of application No. 08/387,813, filed as application No. PCT/CA94/00061, Feb. 3, 1993, Pat. No. 5,695,942, which is a continuation-in-part of application No. 08/012,856, Feb. 3, 1993, abandoned.

[51] Int. Cl.$^6$ .................. G01N 1/00; G01N 1/10
[52] U.S. Cl. .............. 436/180; 436/174; 436/175; 436/177; 436/518; 436/535; 435/7.1; 530/817
[58] Field of Search .................. 436/63, 174–177, 436/180, 518, 524, 528, 529, 534, 535, 823; 435/7.1, 961; 422/68.1; 530/812, 817

[56] References Cited

U.S. PATENT DOCUMENTS

| | | | |
|---|---|---|---|
| 3,495,926 | 2/1970 | Naz | 427/4 |
| 4,255,411 | 3/1981 | Lim et al. | 436/535 |
| 4,280,816 | 7/1981 | Elahi | 436/518 |
| 4,384,193 | 5/1983 | Kledzik et al. | 219/521 |
| 4,731,335 | 3/1988 | Brigati | 436/180 |
| 4,824,791 | 4/1989 | Ekholm et al. | 436/165 |
| 4,908,319 | 3/1990 | Smyczek et al. | 422/99 X |

(List continued on next page.)

FOREIGN PATENT DOCUMENTS

| | | |
|---|---|---|
| 212670 | 3/1987 | European Pat. Off. . |
| 264804 | 4/1988 | European Pat. Off. . |

(List continued on next page.)

OTHER PUBLICATIONS

T. Takahashi et al. *Analytical Biochemistry*, vol. 196, pp. 390–402, 1991.

*Primary Examiner*—Maureen M. Wallenhorst
*Attorney, Agent, or Firm*—Lynn C. Schumacher; Hill & Schumacher

[57] ABSTRACT

There is disclosed an automated apparatus, reagents and process for immunocytochemical staining of biological materials using ligand pairing. The present invention provides a method for storing a ligand in a macroscopic solid support and releasing the ligand into contact with a biological sample mounted on a surface of a substrate. The process includes providing a macroscopic solid support formed of a solidified matrix material encapsulating a ligand therein with the macroscopic solid support being disintegratable to release the ligand therefrom. The solid support is placed in a first chamber which is in flow communication with a second chamber containing the substrate with the biological sample affixed thereto. The step of disintegrating the macroscopic solid support may include heating the macroscopic solid support to liquefy it when the matrix material is gelatin or a wax. An alternative method of disintegrating the solid support is to dissolve it using a solvent such as an aqueous solution added to the first chamber, in this case a water soluble wax is required. The apparatus includes an array of sample cells interconnected with reagent supply and drainage lines. Each cell defines the second chamber or well into which a sample substrate is inserted. The cell includes a cell head defining the first chamber. The chamber in the cell head is in flow communication with the fluid well so that when the ligand is released from confinement in the cell head, the disintegrated solid support flows into the fluid well thereby contacting the mounted biological sample. The ligand support matrix may be gelatin or wax. The cell body and cell head may be differentially heated or cooled so that the mounted sample may be held at the preferred temperature for the reaction of interest and the cell head may be heated to a temperature sufficient to cause thermal degradation of the support.

35 Claims, 5 Drawing Sheets

U.S. PATENT DOCUMENTS

| | | | |
|---|---|---|---|
| 4,985,082 | 1/1991 | Whistler | 127/33 |
| 4,985,206 | 1/1991 | Bowman et al. | 422/99 |
| 5,000,955 | 3/1991 | Gould et al. | 424/497 |
| 5,068,198 | 11/1991 | Gibbons et al. | 436/535 |
| 5,073,504 | 12/1991 | Bogen | 436/174 |
| 5,143,714 | 9/1992 | Cosgrove et al. | 436/535 X |
| 5,413,924 | 5/1995 | Kosak et al. | 435/177 |

FOREIGN PATENT DOCUMENTS

| | | |
|---|---|---|
| 310399 | 4/1989 | European Pat. Off. . |
| 430517 | 6/1991 | European Pat. Off. . |
| 508568 | 10/1992 | European Pat. Off. . |
| 4117830 | 12/1992 | Germany . |
| 8904842 | 6/1989 | WIPO . |

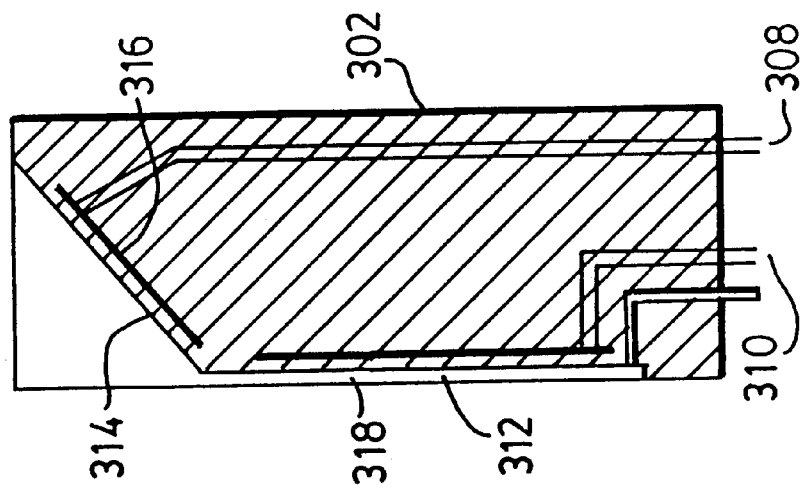
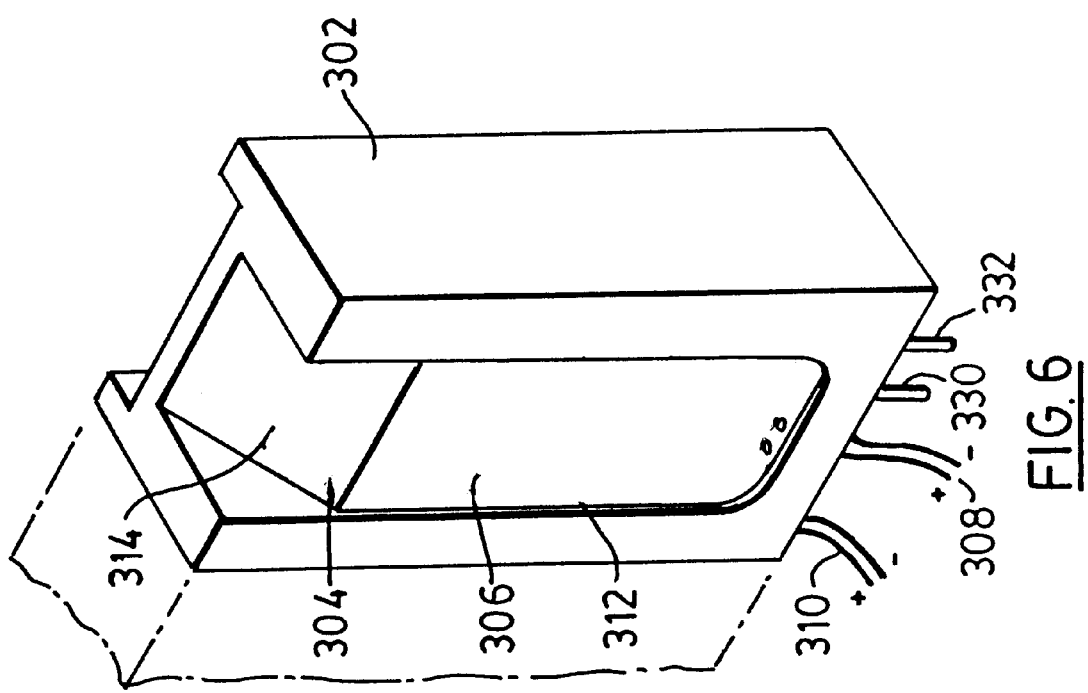

AUTOMATED HISTO-CYTOCHEMISTRY APPARATUS AND ENCAPSULATION SYSTEM FOR PROCESSING BIOLOGICAL MATERIALS

CROSS REFERENCE TO RELATED US PATENT APPLICATIONS

This patent application is a continuation-in-part of U.S. patent application Ser. No. 08/439,315 filed on May 11, 1995 now abandoned, entitled AUTOMATED HISTO-CYTOCHEMISTRY APPARATUS AND ENCAPSULATION SYSTEM FOR PROCESSING BIOLOGICAL MATERIALS, which is a continuation application of U.S. Pat. application Ser. No. 08/387,813 filed on Feb. 28, 1995, now U.S. Pat. No. 5,695,942, issued on Dec. 9, 1997 entitled AUTOMATED HISTO-CYTOCHEMISTRY APPARATUS AND ENCAPSULATION SYSTEM FOR PROCESSING BIOLOGICAL MATERIALS, which is a 371 of PCT/CA94100061 filed on Feb. 3, 1994 in which the United States was designated a continuation-in-part application of U.S. Pat. application Ser. No. 08/012,856 filed on Feb. 3, 1993, now abandoned, entitled AUTOMATED HISTO-CYTOCHEMISTRY APPARATUS AND ENCAPSULATION SYSTEM FOR PROCESSING BIOLOGICAL MATERIALS.

FIELD OF THE INVENTION

The present invention relates to a method, reagents and apparatus for processing biological materials utilizing ligand pairing and relates more particularly to the field of microscopical analysis where one member of a ligand pair is to be detected in a biological sample mounted on a support substrate.

BACKGROUND OF THE INVENTION

To examine the structure of biological samples such as tissues (histology) or cells (cytology), microscopical preparations are made by mounting the sample on a substrate such as a microscope slide. These preparations are routinely stained with dyes to facilitate microscopical examination. To further aid in the identification of the samples, specialized procedures under the general headings of histochemistry (tissue slices) and cytochemistry (biological cell smears) are applied to these preparations. One class of procedures for processing biological materials involves ligand-pair formation wherein a first member of the ligand pair may be present in the biological sample and the other member of the pair binds to the first member when contacted with the sample. Examples of such biologically based ligand-pairs include antibody/antigen couples, lectins/sugars, hormone/receptor systems, enzyme/substrates, DNA/DNA and DNA/RNA couples.

Processing of biological materials involving the antibody/antigen couple forms the basis of immunohistochemistry and immunocytochemistry. Until recently the staining of mounted samples using these reactions has been performed manually. Present machines currently known for immunostaining of samples dispense the antibody containing solutions in liquid form into the fluid well containing the supported sample. These machines require considerable operator attention which entails high labour costs and are prone to suffer from operator error at the stages of dilution, pipetting and loading of reagents. Furthermore, in many circumstances it may be desirable to detect different antigens on an ad hoc basis but the primary antibodies are expensive and prone to deterioration. In addition, the difficulties of working with a large number of small volumes used for a multitude of different tests has acted as a bar to the development of an optimally automated immunocytochemistry staining system.

There are several known methods for storing ligands temporarily. U.S. Pat. No. 5,068,198 issued to Gibbons teaches a temporary confining agent for one member of a specific binding pair (sbp) which is confined in a material to prevent it from combining with the other complementary member of the specific binding pair. Gibbons teaches-the reversible confinement means as being finely divided or particulate, specifically for use in a single liquid medium or reagent wherein the confinement means is suspended to provide for rapid release of the confined sbp member and consequent binding with the nonconfined complementary sbp member present in the liquid medium. The particles may be spherical or irregularly shaped, and normally have average diameters of 10 nm to 500 nm, more usually 20 nm to $2\mu$, frequently 100 nm to $1\mu$. The confinement materials are compatible with and insoluble in the liquid medium, usually an aqueous buffer solution, and are comprised of "immiscible" materials. The principal example taught by Gibbons is liposomes formed such that the outer surface of the liposomes are "substantially free of sbp members." Thus, the confinement means forms a barrier between one member of an sbp enclosed therein and the complementary member of the sbp present in the liquid medium in which the particulate confinement means is suspended.

Although Gibbons' teachings include gels like gelatin as example confinement means, those skilled in the art would recognize that water soluble gels, like gelatin, would be miscible not "immisible" with aqueous buffers. Also, a simple mixture of a water-soluble ligand and a water-soluble confinement means, or other mixtures of ligands and confinement means both soluble in a common solvent, would when formed into particles express the ligand on the particle surface.

U.S. Pat. No. 5,413,924 issued to Kosak is directed to a method of entrapment of liquid reagents such as enzymes or antibodies in wax beads, granules, liposomes and the like which are released upon heating into the surrounding medium such as a solution. The Kosak patent is directed to waxy or wax-like polymers that are essentially water insoluble materials that are solid or semi-solid at room temperature. Although heat-releasable gels, including gelatins are cited as entrapment means, Kosak teaches that heat-releasable gel preparations are dropped through a molten layer of waxy polymer to form beads with a waxy polymer coating to provide a barrier between water-soluble entrapment means and aqueous solutions within or surrounding the entrapment means. Kosak's entrapment means are degradable only by heat. Furthermore, the apparatus disclosed in Kosak is directed to encapsulating droplets of the reagent in wax shell structure to protect the interior from aqueous solvents.

Therefore, a problem of both Gibbons and Kosak is that they teach encapsulation or entrapment means that are designed to be essentially impervious to aqueous solvents, in which most histo-cytochemical reactions take place. It is not possible to apply Gibbons' or Kosak's method of encapsulation with water soluble encapsulation or entrapment media suspended in aqueous media, since these would disintegrate in aqueous solutions.

Accordingly, it is desirable to provide a method, apparatus and reagents for the automated processing of biological materials for histo-cytochemistry and the like, especially for methods involving ligand pairs, which avoids the need to prepare antisera (or other members of specific ligand pairs) immediately prior to use and which does not require accurate positioning and alignment of the sample substrates.

SUMMARY OF THE INVENTION

The solution to the above discussed problem is to form mixtures of ligands with a matrix material that is soluble in the solvent in which the ligand combines with the complementary member of the ligand pair; and which can be formed into a macroscopic solids. Such macroscopic solid supports facilitate long term storage, handling, positioning and alignment of specific reagents for use with and in an automated apparatus.

The present invention provides an apparatus for processing biological materials using ligand pairing, the biological material being mounted on a surface of a substrate. The apparatus comprises a housing provided with at least one cell comprising a first cell portion defining a first chamber having opposed chamber walls. The first chamber is dimensioned to receive the substrate between the opposed chamber walls with the surface of the substrate being adjacent to and spaced from one of the opposed chamber walls a sufficient distance to prevent capillary action from retaining a liquid therebetween. A second cell portion is provided which defines a second chamber adapted to receive a ligand. The second chamber is in fluid flow communication with the first chamber. The apparatus includes reagent supply means for supplying reagent solutions to the first chamber and drainage means for draining said reagent solutions from said first chamber.

In another aspect of the invention there is provided a method of storing a ligand in a releasable containment means. The method comprises providing a matrix material for encapsulating a ligand, the matrix material being soluble in a solvent in which the ligand is functional. The method includes mixing a preselected amount of the ligand with the matrix material, forming a mixture of the ligand and the matrix material, and solidifying the mixture to form a macroscopic solid support encapsulating the ligand which is soluble in a solvent in which said ligand is functional. The macroscopic solid support is responsive to release means to release the ligand therefrom.

In this aspect the matrix material may gelatin and the release means is heat or the solvent, and further, the solvent may be an aqueous solution.

Alternatively, the matrix material may be a solvent-soluble wax and the release means may be heat or the solvent, or the matrix material may be selected from the group consisting of sucrose and starch, and the release means may be an aqueous solution. In another embodiment the matrix material may be glyceryl mono-oleate, and the release means is an aqueous solution having a pH>6.8.

In another aspect of the invention there is provided a method for releasing a ligand stored in a macroscopic solid support into contact with a biological sample mounted on a surface of a substrate. The process comprises the steps of providing a macroscopic solid support comprising a solidified matrix material encapsulating a ligand therein with the macroscopic solid support being disintegratable upon exposure to a release means to release the ligand therefrom. The method includes placing the macroscopic solid support in a first chamber in flow communication with a second chamber holding a substrate having a biological sample affixed to a surface thereof and thereafter disintegrating the macroscopic solid support means by exposing it to the release means. The disintegrated macroscopic solid support means and said released ligand is then flowed into the second chamber into contact with the biological sample.

In this aspect of the invention the step of disintegrating the macroscopic solid support may include heating the macroscopic solid support to melt it forming a melt and flowing the melt into the second chamber under gravity. Further the matrix material may be gelatin or a compatible wax.

Alternatively, in this aspect of the invention the matrix material may be soluble in a solvent in which the ligand is functional. A solvent may be added to the first chamber to dissolve the macroscopic solid support, and the dissolved macroscopic solid support flowed into the second chamber under gravity. Conversely, the solvent may be flowed into the second chamber and a liquid level of the solvent increased so the solvent flows into the first chamber to contact and dissolve the macroscopic solid support.

BRIEF DESCRIPTION OF THE DRAWINGS

The process and apparatus for processing biological materials forming the present invention will now be described, by way of example only, reference being had to the drawings, in which:

FIG. 6 is a perspective view of part of an alternative embodiment of a cell constructed in accordance with the present invention; and FIG. 7 is a cross-sectional side view of the partial cell in FIG. 6.

DETAILED DESCRIPTION OF THE INVENTION

Figure 1:
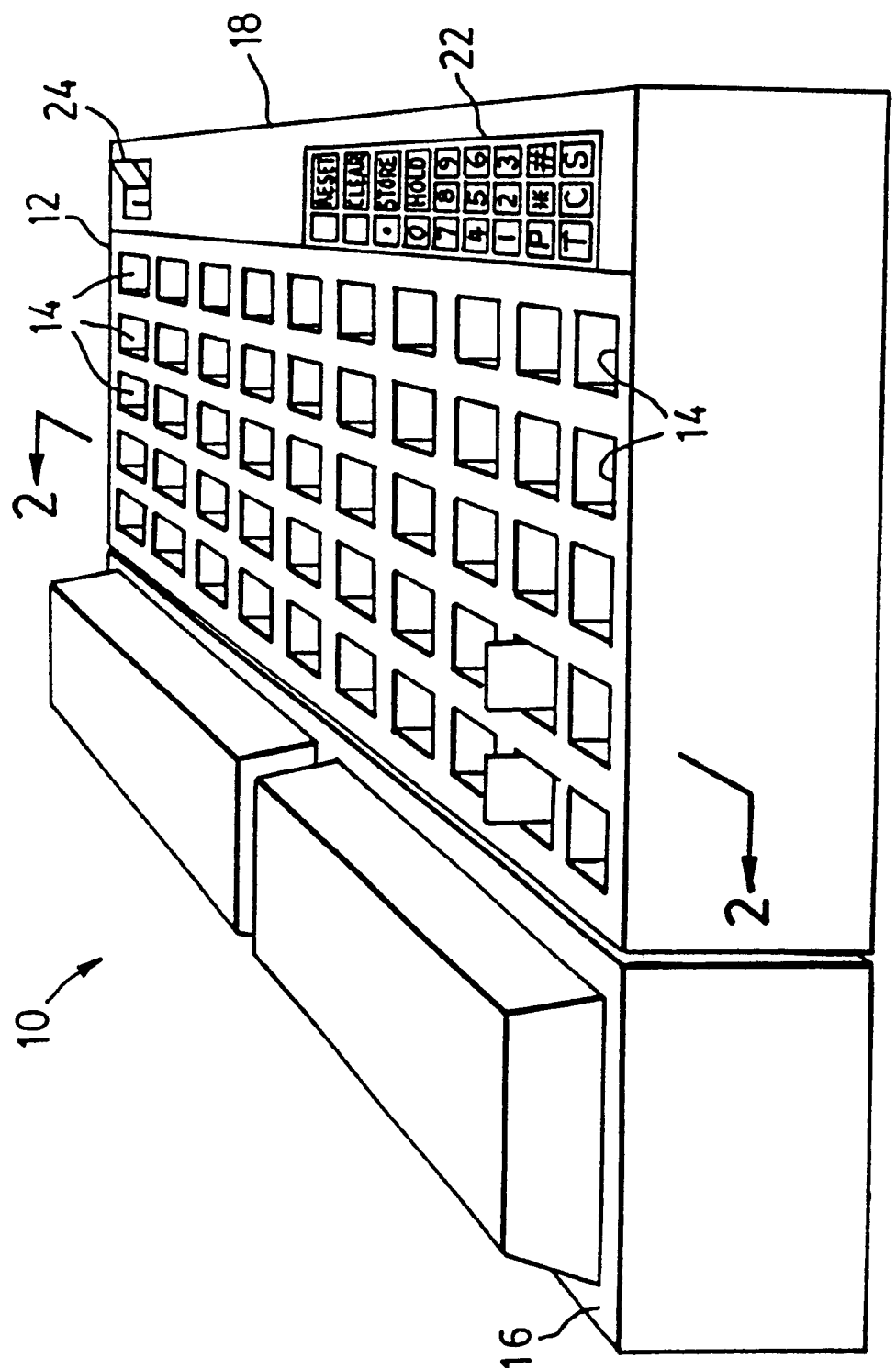
FIG. 1 is a perspective view of an embodiment of an apparatus for processing biological materials forming part of the subject invention.

Referring first to FIG. 1, an automated apparatus 10 for performing the task of processing of biological materials includes a housing or sample compartment 12 comprising a plurality of sample cells 14 arranged in a rectangular array. A storage compartment 16 is located on one side of compartment 12 for housing fluid pumps, valves and reagents and a compartment 18 is located on the other side of compartment 12 for housing electronic control circuitry. An instrument panel comprising a microcomputer keypad 22 and a power switch 24 are shown as part of the control circuitry.

Figure 2:
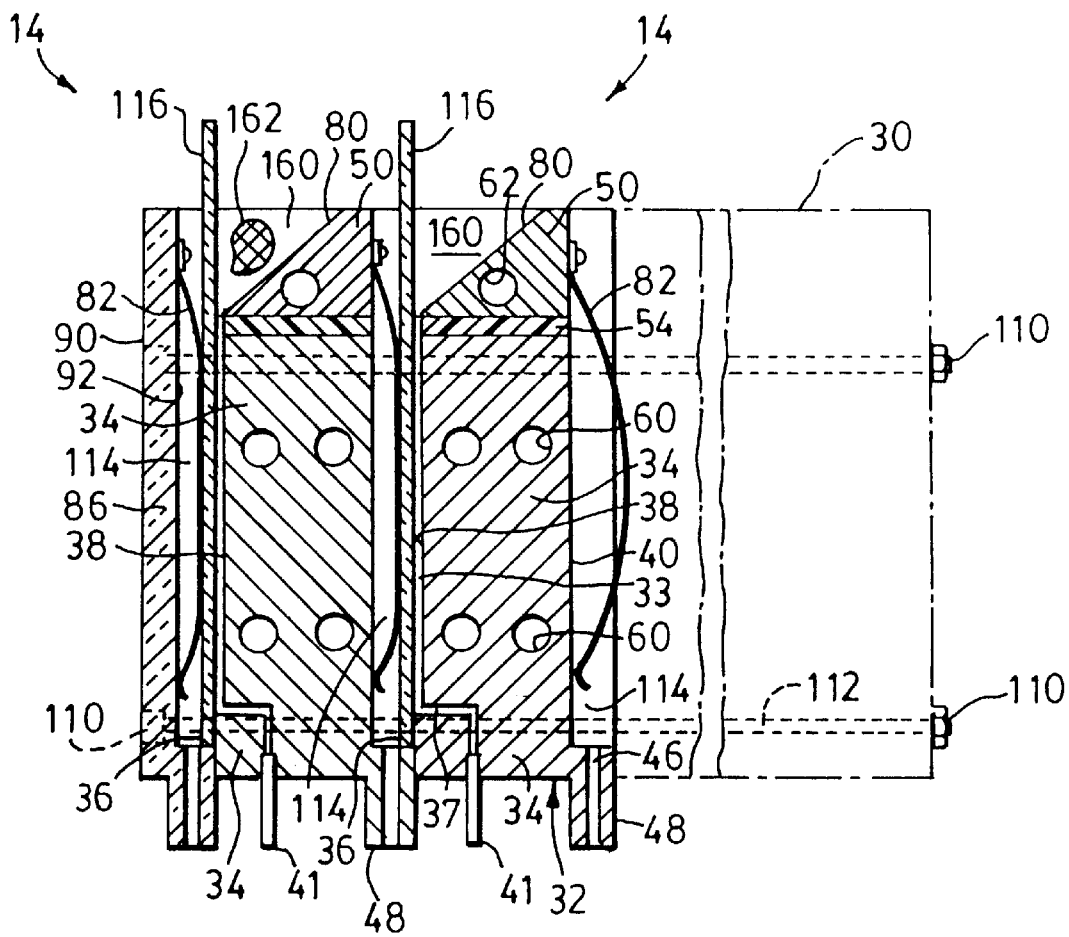
FIG. 2 is a view along the line 2—2 of FIG. 1.
Figure 3:
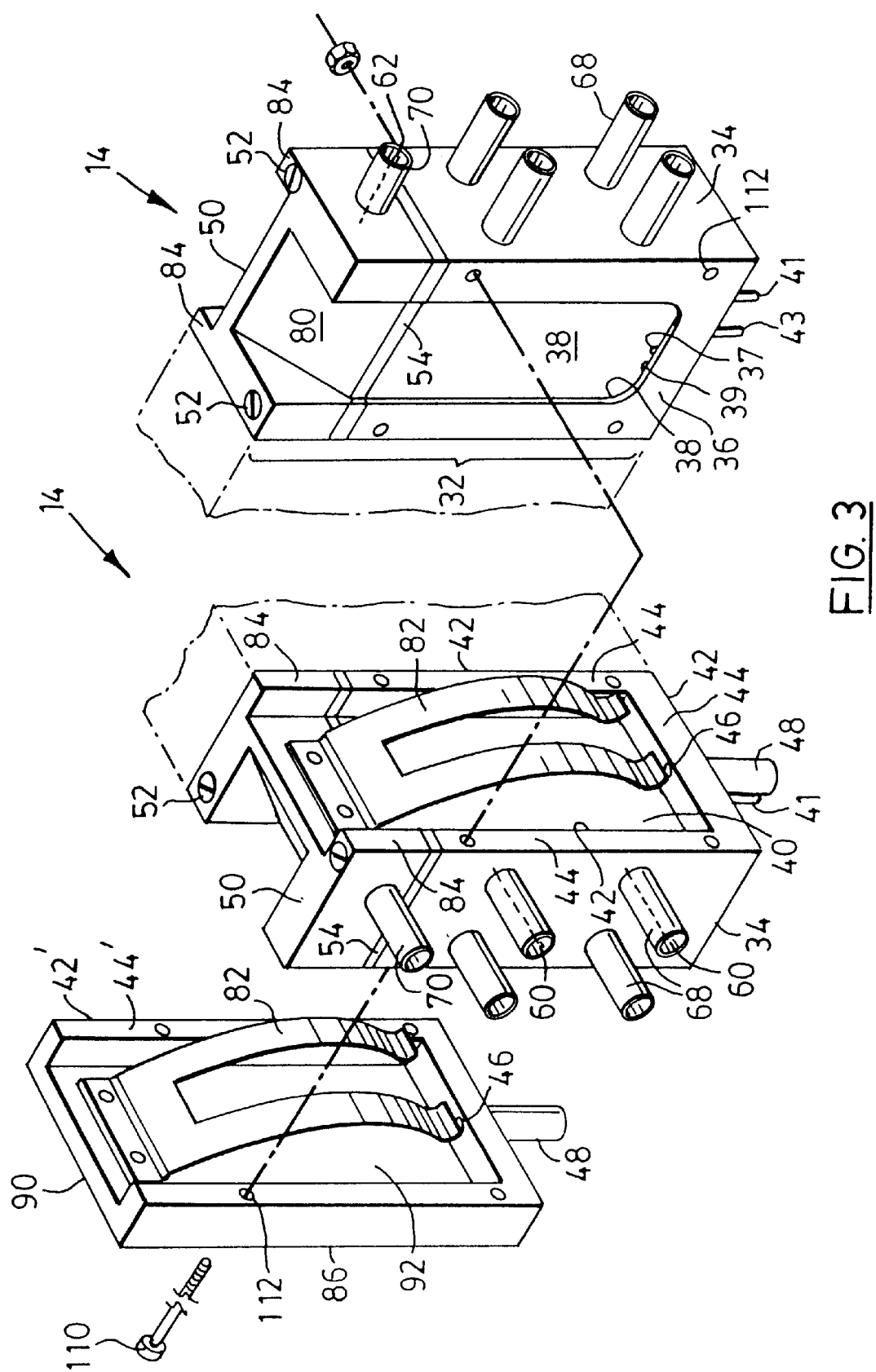
FIG. 3 is a clamshell exploded perspective view of the two cells shown in section in FIG. 2.

Details of sample cells 14 shown in FIG. 1 are more clearly illustrated in FIGS. 2 and 3. Referring specifically to FIG. 3, cells 14 are arranged in rows 30 with each row comprising a plurality of cell blocks 32 attached together. Cell block 32 includes a cell body 34 having on one side thereof a face 36 into which a rectangular shaped recess or well 38 is formed defined by wall 33. Holes 37 and 39 are located along the bottom edge of well 38 and are in flow communication with tubes 41 and 43 respectively which are attached to the bottom of cell body 34 for supplying and draining reagents such as wash buffers to and from the cell.

In another embodiment of the cell, only one hole may be provided (not shown) for both supplying and draining reagents from the chamber. In this arrangement the hole is connected to a tube having a T-junction and valve for providing a reagent inlet and outlet.

The other side of cell body 34 includes a wall 40 having a flange 42 projecting outwardly along three edges thereof. Flange 42 and cell body 34 are dimensioned so that the outer edge 44 of the flange abuts the edges of face 36 of the adjacent cell body 34 when assembled. Cell body 34 includes a liquid overflow comprising a channel 46 extending through the horizontal section of flange 42 and a tube 48 attached to the bottom edge of the flange to drain away liquid.

Cell block 32 is provided with a head portion 50 shown attached to cell body 34 by screws 52. Alternative fastening means such as glues or epoxy may also be used. Cell body 34 and cell head 50 may be fabricated of a metal such as coated aluminum or stainless steel.

Interposed between cell body 34 and head portion 50 is a thermal insulator 54 for thermally insulating the head from the cell body. Insulator 54 may be fabricated of a plastic such as nylon or TEFLON@. Channels 60 extend through cell body 34 and a channel 62 extends through cell head 50. Channels 60 and 62 are provided for passing fluid through the cell components for heating or cooling. Referring to FIG. 3, tubes 68 and 70 are secured to body 34 and head 50 respectively to provide fluid inlets and outlets. Cell body 34 and head 50 may be heated or cooled to the same temperature using a common source of heating fluid or alternatively they may be selectively heated or cooled using separate sources of fluid because of insulator 54 disposed therebetween.

One side of cell head 50 is provided with a surface 80 inclined at about 45 degrees to the horizontal when the cell is assembled. A leaf spring 82 is secured to the other side of cell head 50 coplanar with wall 40 of cell body 34. Spring 82 is bowed outwardly from, and extends downwardly adjacent to, side 40 of cell body 34. The side of head 50 to which spring 82 is attached is provided with flanges 84 projecting outwardly from the side edges, flanges 84 being collinear with the vertical portions of flanges 42 on cell body 34 when the cell head is attached to the body to also sealingly engage face 36. Spring 82 acts to bias substrate 116 against face 36 but other alternative biasing means may be used including a piston arranged to bear against the back surface of the substrate slide.

A front plate 86 is bolted to the adjacent cell block 32 at the front of each row 30. Plate 86 is provided with a planar front face 90 and back face 92 to which spring 82 is attached.

A row of cells is assembled by aligning front plate 86 and a plurality of cell blocks 32 in a row and bolting them together with elongate bolts 110 extending through holes 112 in the plate and similar holes in the cell bodies 34. Alternative means of attaching the cell blocks together may be employed in addition to bolts.

Referring specifically to FIG. 2, each cell 14 is formed when adjacent cell bodies 34 are attached together thereby defining a fluid chamber 114 formed between adjacent cell blocks 32. Chamber 114, which includes well 38, is defined by opposed walls 33 and 40 and is dimensioned to receive substrate 116 with the surface to which the biological material is mounted facing into well 38. Spring 82 acts to bias substrate 116 against cell body 34 with the edges of the substrate overlapping the sides and bottom edge of face 36 on either side of well 38 by about 2 mm to form a seal between the peripheral edge of substrate 116 and face 36.

The internal dimensions of fluid chamber 114 are chosen to ensure that a large enough gap exists between the opposed faces of substrate 116 and the adjacent chamber walls to prevent capillary action. For example, well 38 is of sufficient depth to prevent capillary action from retaining the fluids therein. The minimum allowable dimensions will depend on the material of construction of cell body 34 and on the material wetting properties.

A chamber or receptacle 160 is formed when cell 14 is assembled. Chamber 160 is in flow communication with well 38 when the substrate 116 is in chamber 114. Chamber 160 is dimensioned to receive a support matrix 162 containing a ligand, to be more fully discussed below. Cell head 50 may be constructed with chamber 160 having numerous shapes to act as a receptacle for support matrix 162 as long as there is an unobstructed flow path connecting chamber 160 with well 38.

Figure 4:
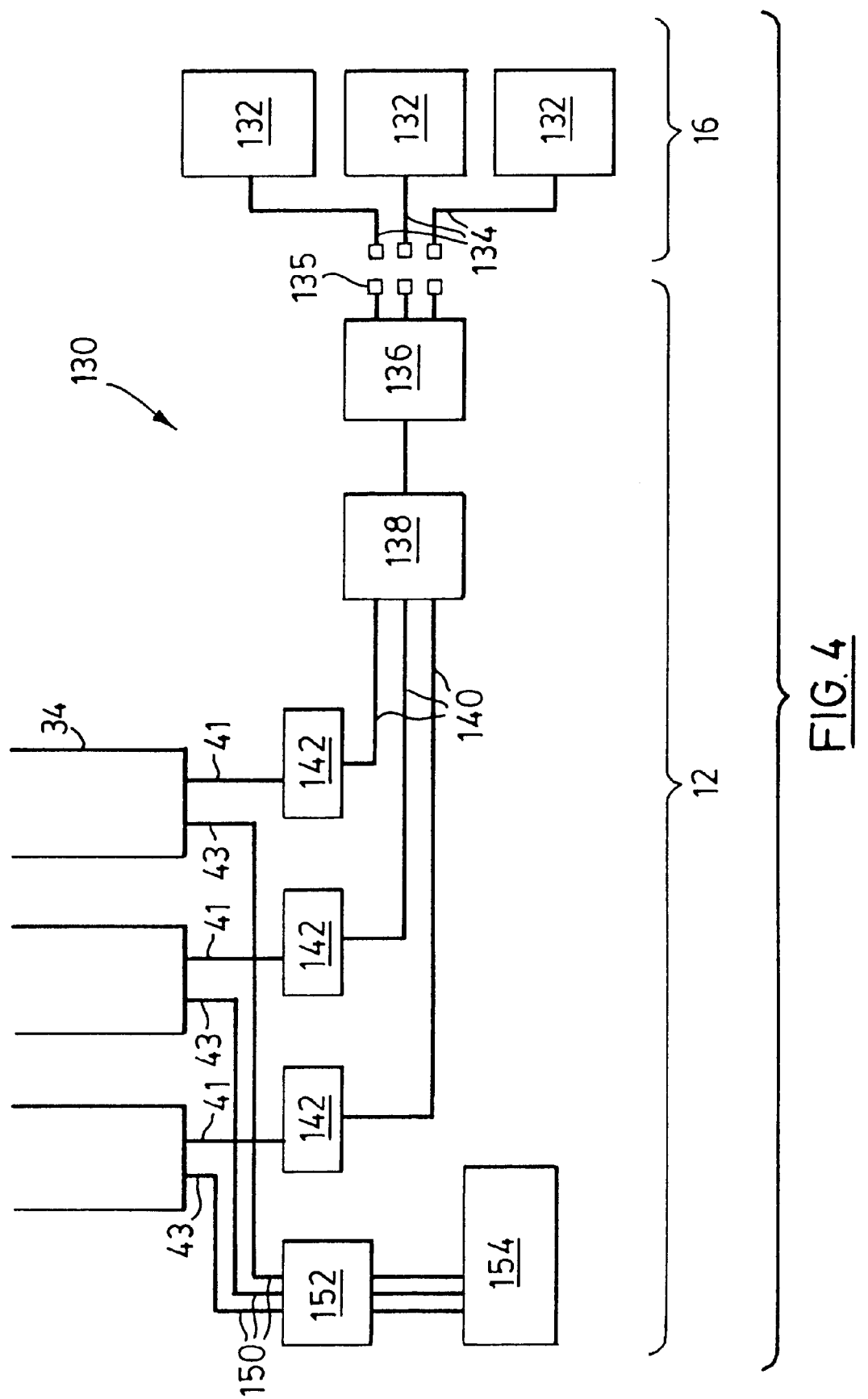
FIG. 4 is a schematic representation of an embodiment of a reagent flow system forming part of the apparatus.

Referring to FIG. 4, a schematic drawing showing one embodiment of a reagent circulation system is shown generally at 130 and comprises a plurality of reagent storage containers 132 stored in reagent storage compartment 16 (FIG. 1). Tubes 134 convey the reagents to the input of a reagent selection valve 136 located within the staining module 12, the output of which is fed to a reagent distribution valve 138. Connectors 135 may be standard snap-fit connectors for conveniently connecting and disconnecting reagent containers 132. A plurality of tubes 140 connect valve 138 with chamber inlet control valves 142, one connected to each tube 41 for supplying reagents to each well 38. Drain tubes 43 are connected to lines 150 which feeds into an outlet valve 152, the output of which is fed to a reagent waste container 154. Other fluid delivery systems will be readily apparent to those skilled in the art. For example, reagent selection valve 136 and reagent distribution valve 138 may be combined into one valve. Alternatively, the function of reagent distribution valve 138 and chamber control valve 142 may be combined into one valve associated with each chamber.

Cell body 34 and head portion 50 may be differentially heated or cooled by water circulated through the body and head by separate pumps and heaters. The pumps and heaters are controlled using standard controllers under microprocessor control. The controllers, pumps and microprocessor may be located in compartments 16 or 18 (FIG. 1) or alternatively may be located external to apparatus 10.

Those skilled in the art will appreciate that numerous other embodiments of apparatus 10 may be made. For example, instead of differentially heating with water, small resistance electrical heaters may be embedded into cell body 34 and cell head 50, the heaters being connected to a dual channel electrical power supply. Standard thermocouples may be attached to the two cell components forming part of the control system.

Substrate 116 may be a standard microscope slide. However, other substrates may be used as well. For example, chamber 114 may be designed to receive substrates comprising an electron microscope grid on which a sample is mounted. Other types of substrates will be readily apparent to those skilled in the art.

Figure 5:
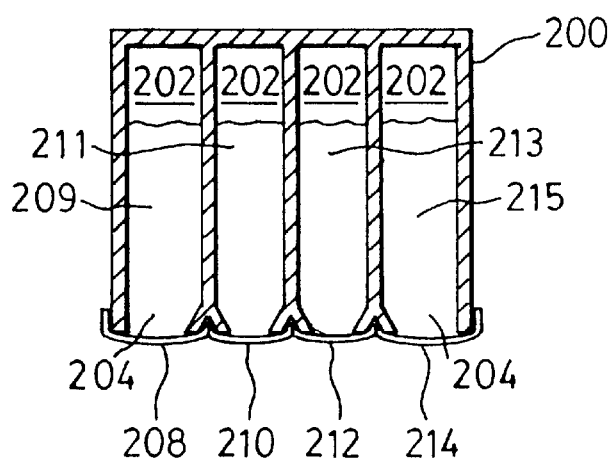
FIG. 5 is a front view of an embodiment of a containing means which may be used with the apparatus forming the subject invention.

Referring to FIG. 5, an alternative containment or confining means 200 comprises a plastic container sized to fit into receptacle 160 as illustrated generally at 200 in FIG. 5. Container 200 comprises a plurality of separate compartments 202 each capable of containing a different solution. At least one of the plurality of separated compartments 202 would contain a solution of a single member of a ligand pair 209, while other compartments may contain solution of an enhancer 211 (i.e. an enzyme solution which enhances results by removing interfering substances) or a solution of one of the several components 213, 215 of the detection system used to detect the ligand previously released and now bound to its complementary partner in the biological material on the substrate. The open ends 204 of each compartment 202 may be sealed with gelatin, wax, plastic or other sheets 208, 210, 212 and 214 which melt at the same or different temperatures or may be broken by other physical means depending on the application for which the ligand pair members are being used.

Referring now to FIGS. 6 and 7, an alternative cell body 302 has a cell head 304 integrally formed therewith as a single unitary piece. Cell body 302 and head 304 are fabricated of a low thermally conductive material such as TEFLON® or nylon. Cell body 302 includes a well 312 defined by wall 306. Cell head portion 304 includes an inclined surface 314 which acts as a receptacle into which a releasable containment means is inserted in use. Head portion 304 is heated by a heater element 316 embedded below inclined surface 314. Electrical conductors 308 provide power to heater 316. Cell body 302 is by a heater element 318 embedded in the body below wall 306. Conductors 310 provide power to heater 318. Cell body 302 and cell head 304 may be selectively heated in this way because cell block 302 is made of a low thermally conductive material.

The fully automated system disclosed herein is advantageous in that it allows the concurrent demonstration of many different antigens when processing the biological samples with antibody/antigen systems. FIG. 1 illustrates an embodiment of the apparatus comprising 50 cells 14 but machines may be constructed with more or less cells depending on the anticipated load for the particular application. Apparatus 10 may house adequate stocks of the appropriate solvents, normal sera, secondary and tertiary immuno-labelling reagents and colour developing solutions. In one embodiment the apparatus may comprise a refrigeration unit for the pre-diluted primary and accessory antibodies in order to allow storing of reagents.

The set-up procedure comprises the three steps of: 1) placement of the substrates having the biological samples mounted thereon into cells 14; 2) inserting into chamber 160 a releasable containment means 162 containing at least one member of a ligand pair to be contacted with the biological sample; and 3) initiating the start sequence. The apparatus may be adapted to perform the steps of: blocking endogenous enzyme activity (for peroxidase labelling systems); proteolysis; blocking non-specific protein binding; multiple antibody incubations with intervening washes; colour development; and possibly counterstaining. The substrates are then manually removed from the machine for coverslipping and microscopical examination. Biological samples in the form of paraffin sections may be manually dewaxed prior to insertion into chamber 114, or alternatively the apparatus may be adapted to perform the steps of dewaxing and hydration. Specifically, with appropriate tubing, electrical insulation and locating the apparatus in a properly ventilated area, the steps of automated dewaxing and hydration of paraffin sections could be performed using known dewaxing and hydration agents such as xylene and alcohol solutions.

In operation, substrate 116, which supports a biological sample on one surface thereof, is inserted into chamber 114 with the sample facing well 38. A releasible macroscopic solid support 162 (containing a ligand the other member of the pair) is placed in chamber 160. The step of disintegrating the macroscopic solid support may be heating the macroscopic solid support to melt it forming a melt and flowing the melt into the lower chamber 160 under gravity.

Alternatively, the matrix material may be soluble in a solvent in which the ligand is functional. A solvent may be added to the first chamber to dissolve the macroscopic solid support, and the dissolved macroscopic solid support flowed into the second chamber under gravity. Conversely, the solvent may be flowed into the second chamber and a liquid level of the solvent increased so the solvent flows into the first chamber to contact and dissolve the macroscopic solid support.

Chamber 160 is positioned such that the solvents delivered into fluid chamber 114 do not make contact with solid support 162, other than for release of the contained ligand which can be effected by raising the level of the solvent so it enters chamber 160 and dissolves support 162. Thus, the containment means is used to retain the ligand in a compartment physically separate for the fluid chamber 114, in which all steps of the reaction process occur. The matrix material is formulated such that the subsequently released reagent is soluble in and miscible with the solvent in which the substrate in fluid chamber 114 is or was immediately beforehand immersed. The containment volume of the releasable containment means is generally greater than 50 $\mu L$, more usually in the range of 100 $\mu L$ to 300 $\mu L$, and for the embodiment of the instrument described herein, optimally 200 $\mu L$.

The disintegrated macroscopic solid support can be drawn down into chamber 160 by draining the solvent out of chamber 160 and letting the dissolved mixture in chamber 162 flow by gravity into chamber 160 or alternatively suction can be applied on chamber 160 to draw the mixture down from chamber 162.

When used with the apparatus having heated components, macroscopic solid support 162 is preferably comprised of a gelatin or wax solid matrix material to be described in more detail below. Alternatively, macroscopic solid support 162 may comprise a hollow capsule. The gelatin and wax matrices are temperature sensitive so that at a certain predetermined temperature the matrix thermally degrades to release its contents. Hollow capsules are released by alternative release means such as puncture, pressure, vacuum and electricity. Cell body 34 is maintained at the optimum temperature for rapid and specific ligand pairing procedures. Once the support matrix/capsule 162 has been placed in cell head 50, the temperature of the head may be raised at some point during the procedure, so that the macroscopic solid support or capsule breaks down thereby releasing the reagent contained therein. The reagent and matrix material then flow onto the substrate, being soluble and miscible with any solvent in which the substrate is or was immediately beforehand immersed.

The matrix material may be made of a material which can be broken down or decomposed by any one of several physical or chemical processes such as by puncture, electrical, pressure, vacuum or exposure to EM radiation or solvents.

For example, when the matrix material is sucrose or starch (amylose or amylopectin) containing antibodies, decomposition may be achieved by exposure to aqueous or aqueous buffered solutions so that head portion 50 need not be heated. When selecting a matrix material system for a given ligand, it is important that the ligand and matrix material do not irreversibly bind. Moreover, when using solid or semi-solid matrices, the support material must be miscible with the solvent (usually water) employed for the reaction procedure.

Alternatively, chemical processes such as degradation or pH change may be utilized as a release means to break down the matrix, this being accomplished by filling fluid well 38 and chamber 160 with a suitable reagent. When the matrix material is glyceryl mono-oleate (MYVEROL 18–99®) then decomposition may be effected by exposure to solutions of pH>6.8. Release of DNA probes linked to a solid matrix through disulphide bonds may be achieved by dithiothreitol cleavage. Release of DNA probes bound to a solid matrix may also be effected by enzyme release through nuclease-specific auxiliary sequences.

One criterion for selecting the chemical release means is that the other components of the biological system are not adversely affected or interfered with by the chemical. The result of breaking down the matrix is to release the preservative medium containing the solution of antibodies from confinement in a physical compartment separate from the substrate. The solutions then flow through the fluid flow path through the cell into contact with the biological sample mounted on the substrate.

When the apparatus is used for immunocytochemical staining applications, the reagent encapsulated within the capsule comprises stabilized antibodies and is more fully discussed herebelow. However, apparatus 10 may be used for other applications involving the pairing of initially separate ligand pairs. Non-limiting examples of such ligand pairs includes lectins/sugars, hormone/receptor systems, enzyme/substrates, DNA/DNA and DNA/RNA couples to mention a few. The member of the ligand pair to be detected in a sample is mounted on substrate 116 within chamber 114 with the sample facing well 38 and the complementary member of the ligand pair is contained within a support matrix/capsule 162 mounted in chamber 160.

Antibody Stabilization And Support

The highly specific nature of antibodies (or immunoglobulins) for recognizing different antigens forms the basis for immunocytochemistry (immunohistochemistry). In this technique the antigen of interest to be identified in biological samples is purified and an animal is immunized with the antigen thereby eliciting the synthesis of the specific antibodies. These antibodies may then be isolated and applied in-vitro to the sample. The antibodies bind to a site on the recognizable antigen in the sample and the resulting complexes may be detected by light microscopy using labels such as fluorochromes, enzymes such as horseradish peroxidase and alkaline phosphate which in turn may be detected using histochemical reactions or colloidal metal particles which are detected using electron microscopy.

The antibodies are stabilized by being dissolved in a suitable stabilizing medium which in turn is releasably contained within a solid support matrix or capsule. The matrix may be a solid gelatin, water-soluble wax or alternative solvent-miscible block or a hollow capsule made of plastic or the like, which encapsulates the stabilizing medium containing the primary antibodies. The stabilizing medium may comprise a saline solution with a buffering system such as TRIZMA® based buffers, phosphate based buffers, citrate based buffers and the like. The stabilizing medium may also comprise detergents such as TRITON X-100® (octyl phenoxy polyethoxy ethanol), NP40® (octyl phenol ethylene oxide condensate), TWEEN 20® (polyoxyethylene sorbitan monolaurate) and TWEEN 80® (polyoxyethylene sorbitan mono-oleate as well as biological compounds such as proteins, glycolipids, glycoproteins and antimicrobial agents such as thimerosal, sodium azide, sodium metabisulphite and the like. Gelatin is the preferred confining medium for the above referenced solutions while water-soluble wax is preferred for simple aqueous antibody solutions. Several examples of encapsulation systems are now described.

EXAMPLE I

In this application, a solution of antibodies in suitable stabilizing medium is incorporated into a gelatin matrix with appropriate physical properties and sensitive to melting by heat at temperatures in for example the 35–45° C. range. This matrix has been tested for compatibility with the antibodies, and is composed of a 6% gelatin (300 bloom) in antibody preserving solution. The antibody in gelatin matrix is formed into a convenient form, and solidified by reducing the temperature. The gelatin matrix may then be handled, shipped, stored, etc. To release the antibodies, the gelatin matrix is destroyed by heating to about 40° C. The matrix melts to form a gelatin/buffer solution which may flow into empty well 38 or mix with a reagent solvent or buffer previously admitted into the well through inlet tube 41 from the reagent supply. The matrix is formulated to ensure solubility and miscibility with the solvent or buffer (usually aqueous) previously admitted to the well. Alternatively, the reagent buffer in well 38 may be displaced into chamber 160 by the gelatin/buffer solution or it may be pumped out.

EXAMPLE II

In this application, the antibodies and subsequent reagents are incorporated into multiple gelatin or wax matrices which melt at temperatures in the 35–50° C. range. They are formed into a convenient physical shape, and the reagents are released as in Example I by heating and melting the matrix. In this case, the different matrices are melted at different temperatures, reagent 1 is in a matrix melted at about 40° C., reagent 2 is in a matrix melted at about 45° C., and reagent 3 is in a matrix melted at about 50° C.

Example III

This example is similar to Examples I & II in that the different reagents are released by melting matrices which are sensitive to different temperature ranges. However, the reagents are in a liquid or semi-solid solution which is held in a capsule barrier. A physical means such as puncture, pressure, vacuum or electricity destroys the barrier, and the reagent is released into the buffer solution in the well and reacts with the sample.

Those skilled in the art will appreciate that the method of supporting one member of a ligand pair in a support matrix forming part of the present invention is not limited to use with the automated apparatus also forming part of the present invention. For example, the support matrix containing one member of the ligand pair may be placed on a substrate having a sample mounted thereon. The release means, whether heat, solvent etc. is then applied to the support matrix to release the ligand member therefrom to contact it with the sample.

Therefore what is claimed is:

1. A method of storing a ligand in a releasable containment means, comprising:

providing a matrix material for encapsulating a ligand, the matrix material being soluble in a solvent in which said ligand is functional; and mixing a preselected amount of said ligand with said matrix material, forming a mixture of said ligand and said matrix material, and solidifying said mixture to form a macroscopic solid support encapsulating said ligand which is soluble in a solvent in which said ligand is functional, said macroscopic solid support being responsive to release means to release said ligand therefrom.

2. The method according to claim 1 wherein said matrix material is gelatin and said release means is heat.

3. The method according to claim 1 wherein said matrix material is gelatin and said release means is an aqueous solution.

4. The method according to claim 1 wherein said matrix material is a wax and said release means is heat.

5. The method according to claim 1 wherein said matrix material is a solvent soluble wax and said release means is an effective solvent.

6. The method according to claim 5 wherein said matrix material is a water soluble wax and said release means is an aqueous solution.

7. The method according to claim 1 wherein said matrix material is selected from the group consisting of sucrose and starch, and the release means is an aqueous solution.

8. The method according to claim 1 wherein said matrix material is glyceryl mono-oleate, and the release means is an aqueous solution having a pH greater than about 6.8.

9. A method for releasing a ligand stored in a macroscopic solid support into contact with a biological sample mounted on a surface of a substrate, the method comprising the steps of:

providing a macroscopic solid support comprising a matrix material encapsulating a ligand therein, said macroscopic solid support being disintegratable upon exposure to a release means to release said ligand therefrom;

placing said macroscopic solid support in a first chamber in flow communication with a second chamber holding a substrate having a biological sample affixed to a surface thereof, said second chamber having a gap between opposed chamber walls large enough to avoid capillary action within said second chamber; and disintegrating said macroscopic solid support by exposing it to said release means and flowing said disintegrated macroscopic solid support and said released ligand into said second chamber into contact with said biological sample.

10. The method according to claim 9 wherein said step of disintegrating said macroscopic solid support includes heating the macroscopic solid support.

11. The method according to claim 10 wherein said disintegrated solid support is flowed from said first chamber to said second chamber under gravity.

12. The method according to claim 10 wherein said disintegrated macroscopic solid support is flowed from said first chamber to said second chamber by applying suction to said second chamber to draw the disintegrated macroscopic solid support into said second chamber.

13. The method according to claim 10 wherein said disintegrated macroscopic solid support is flowed from said first chamber to said second chamber by applying pressure to said first chamber.

14. The method according to claim 9 wherein said matrix material is gelatin.

15. The method according to claim 9 wherein said matrix material is a wax.

16. The method according to claim 9 wherein said matrix material is disintegrated in a solvent in which said ligand is functional.

17. The method according to claim 16 wherein said solvent is added to said first chamber to dissolve said macroscopic solid support.

18. The method according to claim 17 wherein said solvent containing the dissolved macroscopic solid support is flowed from said first chamber to said second chamber under gravity.

19. The method according to claim 17 wherein said solvent containing the dissolved macroscopic solid support is flowed from said first chamber to said second chamber by applying suction to said second chamber to draw the dissolved macroscopic solid support into said second chamber.

20. The method according to claim 17 wherein said solvent containing the dissolved macroscopic solid support is flowed from said first chamber to said second chamber by applying pressure to said first chamber.

21. The method according to claim 16 wherein said solvent is flowed from said second chamber into said first chamber to dissolve said macroscopic solid support.

22. The method according to claim 16 wherein said matrix material is gelatin and said solvent is an aqueous solution.

23. The method according to claim 16 wherein said matrix material is a wax soluble in said solvent.

24. The method according to claim 16 wherein said solvent is an aqueous solution and said matrix material is a water soluble wax.

25. The method according to claim 16 wherein said matrix material is selected from the group consisting of sucrose and starch, and the solvent is an aqueous solution.

26. The method according to claim 16 wherein said matrix material is glyceryl mono-oleate, and the solvent is an aqueous solution with a pH greater than about 6.8.

27. A method for releasing a ligand stored in a macroscopic hollow support into a solvent in contact with a biological sample mounted on a surface of a substrate, the method comprising the steps of:

providing a macroscopic hollow support containing a ligand dissolved in a first solvent and placing said macroscopic hollow support in a first chamber in flow communication with a second chamber holding a substrate having a biological sample affixed to a surface thereof, said second chamber having a gap between opposed chamber walls large enough to avoid capillary action within said second chamber; and disintegrating said macroscopic hollow support by exposing it to a release means and flowing said first solvent containing said dissolved ligand into said second chamber into contact with said biological sample.

28. The method according to claim 27 wherein said release means for disintegrating said macroscopic hollow support includes physical disruption of said macroscopic hollow support.

29. The method according to claim 28 wherein said macroscopic hollow support is a pressure-sensitive capsule and said physical disruption is pressure.

30. The method according to claim 28 wherein said macroscopic hollow support is a vacuum-sensitive capsule and said physical disruption is vacuum.

31. The method according to claim 28 wherein said macroscopic hollow support is a puncturable capsule and said physical disruption is puncture.

32. The method according to claim 28 wherein said macroscopic hollow support is an electrical current-sensitive capsule and said physical disruption is electrical current.

33. The method according to claim 27 wherein the solvent containing the dissolved ligand from the disintegrated macroscopic hollow support is flowed from said first chamber to said second chamber under gravity.

34. The method according to claim 27 wherein the solvent containing the ligand from the disintegrated macroscopic hollow support is flowed from said first chamber to said second chamber by applying suction to said second chamber to draw the solvent into said second chamber.

35. The method according to claim 27 wherein said solvent containing the ligand from the disintegrated macroscopic hollow support is flowed from said first chamber to said second chamber by applying pressure to said first chamber.

* * * * *